United States Patent [19]

Hamada et al.

[11] 4,403,294

[45] Sep. 6, 1983

[54] SURFACE DEFECT INSPECTION SYSTEM

[75] Inventors: Toshimitsu Hamada; Hiroshi Makihira; Yasuo Nakagawa, all of Yokohama; Makoto Udaka, Yokosuka, all of Japan

[73] Assignees: Hitachi, Ltd.; Japan Nuclear Fuel Co., Ltd., both of Tokyo, Japan

[21] Appl. No.: 211,113

[22] Filed: Nov. 28, 1980

[30] Foreign Application Priority Data

Nov. 30, 1979 [JP] Japan .............................. 54-154413

[51] Int. Cl.³ .......................................... G01N 21/48
[52] U.S. Cl. .................................. 364/507; 358/106; 356/237; 250/562
[58] Field of Search ...................... 364/507, 515, 525; 358/101, 106, 107; 356/430, 431, 237, 239; 250/202, 562, 563, 572; 340/146.3 AC, 146.3 AE

[56] References Cited

U.S. PATENT DOCUMENTS

| 3,887,762 | 6/1975 | Uno et al. .......................... 358/106 |
| 3,988,530 | 10/1976 | Ikegami et al. ..................... 356/430 |
| 4,110,048 | 8/1978 | Akutsu et al. ...................... 356/431 |
| 4,110,736 | 8/1978 | Kono .......................... 340/146.3 AE |
| 4,148,065 | 4/1979 | Nakagawa et al. ................. 358/106 |
| 4,162,126 | 7/1979 | Nakagawa et al. ................. 356/237 |
| 4,173,441 | 11/1979 | Wolf ................................... 356/431 |
| 4,183,013 | 1/1980 | Agrawala et al. ........ 340/146.3 AC |
| 4,223,346 | 9/1980 | Neiheisel et al. .................. 356/430 |
| 4,237,539 | 12/1980 | Piovoso et al. ..................... 250/562 |

Primary Examiner—Gary Chin
Attorney, Agent, or Firm—Antonelli, Terry & Wands

[57] ABSTRACT

A surface defect inspection system comprises an image pick-up device for picking up an image by sequentially scanning the surface of an object two-dimensionally, a threshold circuit for quantizing the image signal produced from the image pick-up device as a binary code, a pattern feature extracting device for making calculations for extracting the features of image patterns from the quantized signal in synchronism with the scanning, and for temporarily storing the result of the calculations, a pattern region end decision device for deciding that individual pattern regions have ended in one direction, and a defect decision device for reading out from the pattern feature extracting device the result of the calculations on the pattern features corresponding to the positions each of the patterns in the direction perpendicular to the one direction each time of the decision that each pattern region has ended, so that the feature of each pattern scanned is compared with a predetermined reference, thus deciding and an indication of producing the presence or absence of a defect.

12 Claims, 19 Drawing Figures

SURFACE DEFECT INSPECTION SYSTEM

The present invention relates to a system for inspecting surface defects of an object, applicable to automatic appearance inspection in which the presence or absence, for instance, of a pit (a small hole caused by corrosion or the like) or a crack in the surface of a metal is automatically detected, and further whether a detected pit or crack is a tolerable defect is automatically decided.

Figure 1:
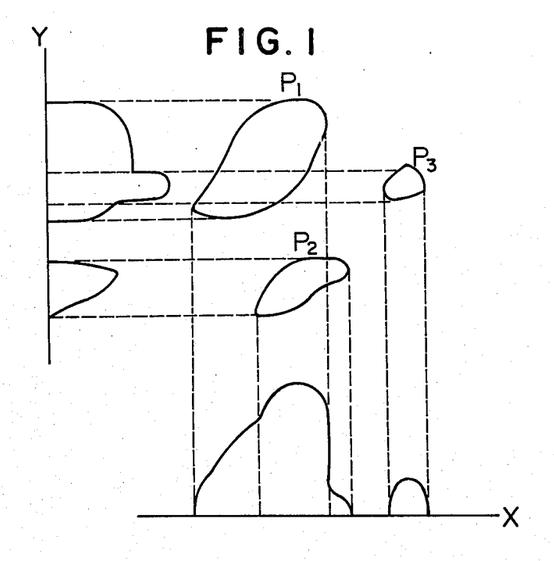
FIG. 1 is a diagram for explaining an example of decision by a conventional system.

In a conventional surface defect inspection system, an image of the surface of an object is obtained by an image pick-up device, so that the features of the pattern of the image such as the area, longitudinal and cross lengths and width thereof are used as factors for decision. A conventional system is shown in FIG. 1. The shadow distribution of the image patterns $P_1$, $P_2$ and $P_3$ projected on the screen along the X axis and the shadow distribution along the Y axis are obtained, whereby a pattern feature is extracted. In this conventional system, the pattern extraction is impossible or very difficult in the case where a plurality of independent patterns exist on a single screen as shown in FIG. 1.

Accordingly, it is the object of the present invention to provide a surface defect inspection system capable of eliminating the above-mentioned disadvantage of the prior art system.

According to the present invention, there is provided a surface defect inspection system comprising image pick-up device for picking up an an image by sequentially scanning the surface of an object two-dimensionally, a threshold circuit for quantizing the image signal produced from the image pick-up means as a binary code, a pattern feature extracting device for making calculations for extracting the feature of image patterns from the quantized signal in synchronism with the scanning, and for temporarily storing the result of the calculations, a pattern region (shadow region along one axis) end decision means for deciding that individual pattern regions have ended in one direction, and a defect decision device for reading out from the pattern feature extracting device the result of the calculations on the pattern features corresponding to the positions of each of patterns in the direction perpendicular to the one direction each time of the decision that each pattern region has ended, so that the feature of each pattern scanned is compared with a predetermined reference, thus deciding and producing the presence or absence of a defect.

The above and other objects, features and advantages will be made apparent by the detailed description taken in conjunction with the accompanied drawings, in which.

The present invention will be described with reference to the accompanying drawings.

Figure 2:
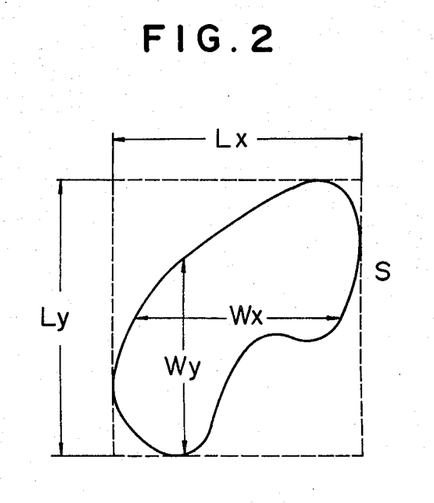
FIG. 2 is a diagram showing the features of a pattern extracted in a specific example of the present invention.

The features of a pattern employed include the pattern area S, the lengths Lx and Ly along the X and Y axes, and the widths Wx and Wy along the X and Y axes. An embodiment will be described on the assumption that a pattern defect is decided by determining these features of a pattern. The features of the pattern are shown in FIG. 2. The lengths Lx and Ly of the pattern along the X and Y axes represent the lengths of the longitudinal and lateral sides of a two-dimensional rectangular region in which the pattern exists. The widths Wx and Wy along the X and Y axes of the pattern, on the other hand, represent the maximum values of horizontal and vertical widths of the pattern itself. When a pattern has ended, it means that the pattern has ceased to exist in the part covered by the length Lx along the X axis where the pattern has thus far been present. According to the present invention, the features of each pattern in the direction of a scanning line are determined to decide a defect each time the pattern region ends in the direction perpendicular to the scanning line.

Figure 3:
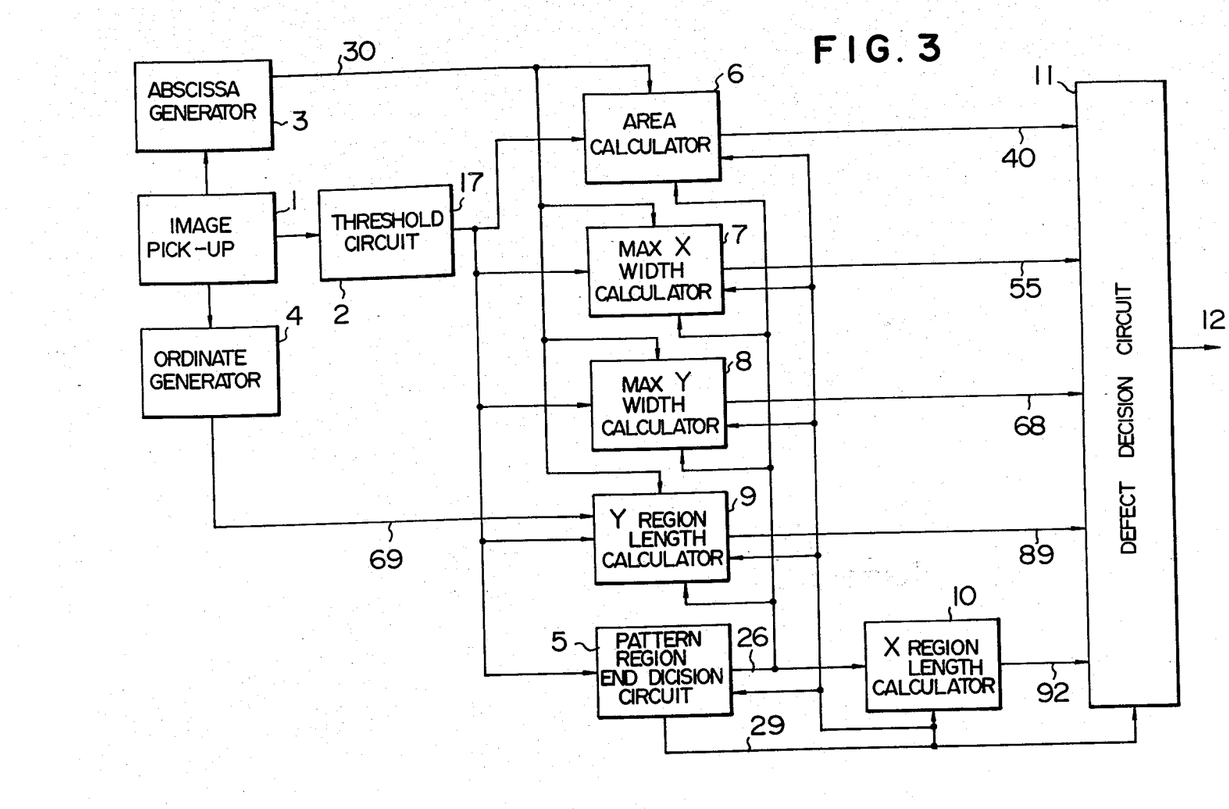
FIG. 3 is a block diagram showing the general configuration of an embodiment of the present invention.

The general configuration of an embodiment of the present invention is shown in the block diagram of FIG. 3. In this diagram, reference numeral 1 shows an image pick-up device for scanning the surface of an object along the X axis while at the same time being fed along the Y axis thereby to pick up an image two-dimensionally. The image pick-up device 1 is specifically constructed as disclosed in U.S. patent application Ser. No. 170180 filed July 18, 1980 assigned to the same assignee as that to the present invention. Numeral 2 shows a threshold circuit for quantizing the image pattern obtained by the image pick-up device 1. Numerals 3 and 4 are an abscissa generator circuit and an ordinate generator circuit respectively for calculating the coordinate of the scanning position of the image pick-up device 1. Numeral 5 shows a pattern region end decision circuit for deciding a pattern region end in response to a quantized signal from the threshold circuit 2. "1" or "0" pattern signals continue in the pattern region in the ordinate direction. Numeral 6 shows an area calculator circuit for calculating the pattern area S in response to the quantized signal from the threshold circuit 2 and the abscissa signal from the abscissa generator circuit 3. The area of each pattern is calculated by the output signal of the pattern end decision circuit. Numeral 7 shows a maximum X width calculating circuit for calculating the maximum width Wx of the pattern along the X axis. The maximum width of each pattern along the X axis is calculated by the output signal of the pattern end decision circuit 5 in response to the quantized signal and the abscissa signal. Numeral 8 shows a maximum Y width calculating circuit for calculating the maximum width Wy of the pattern along the Y axis. The maximum width of each pattern along the Y axis is calculated on the basis of the output signal of the pattern region end decision circuit 5 in response to the quantized signal and the abscissa and ordinate signals. Numeral 9 shows a Y region length calculating circuit for determining the region length Ly of the pattern along the Y axis. The region length of each pattern along the Y axis is calculated by the output signal of the pattern end decision circuit 5 in response to the quantized signal, the abscissa signal and the ordinate signal. Numeral 10 shows an X region length calculating circuit for calculating the region length Lx of the pattern along the X axis in response to the output signal of the pattern region end decision circuit 5. Numeral 11 shows a defect decision circuit for deciding on a defect and producing a decision result signal 12 in response to the features of each pattern which are collected by the output signal of the pattern region end decision circuit 5.

Figure 4:
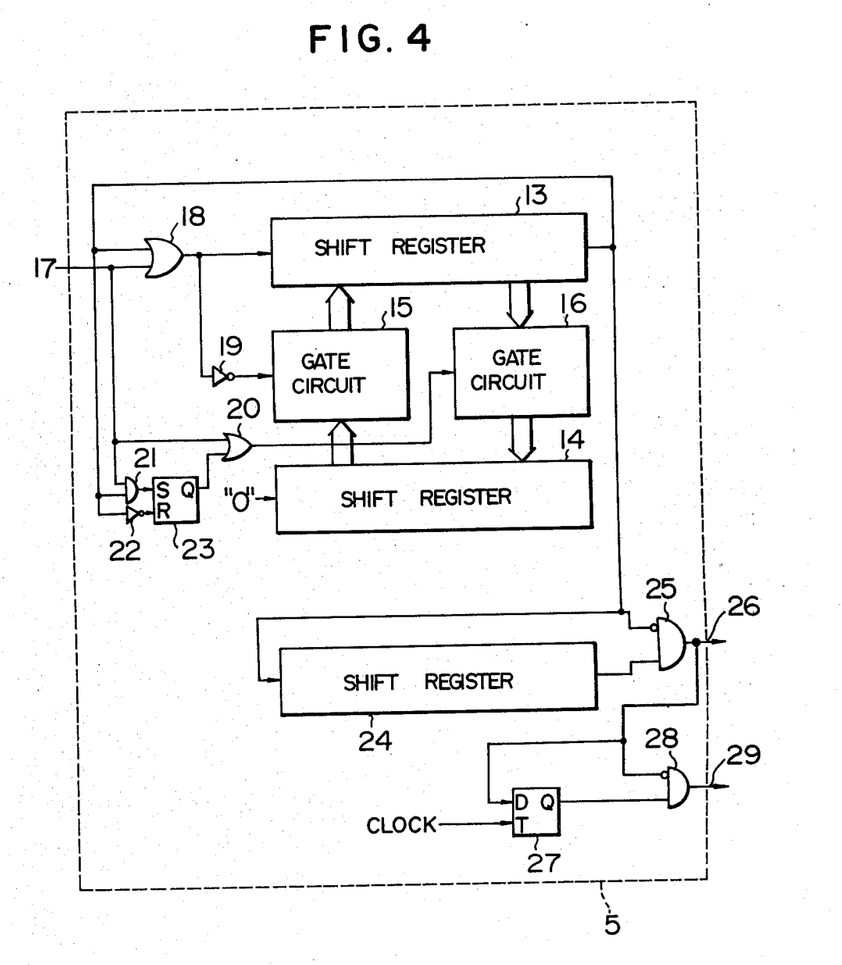
FIG. 4 is a diagram showing an embodiment of a pattern end decision circuit in FIG. 3.

An embodiment of the pattern region end decision circuit 5 of FIG. 3 is shown in FIG. 4. In this diagram, numerals 13 and 14 show parallel-in parallel-out shift registers respectively the length of which correspond to the length of the scanning line of the image pick-up device 1 of FIG. 3. All the data stored in these shift registers 13 and 14 are rewritten from the former to the latter or from the latter to the former through gate circuits 15 and 16. The shift register 13 is supplied with the quantized signal 17 from the threshold circuit 2 (FIG. 3) and the output signal of the shift register 13 itself through an OR gate 18, and the shift register 14 is supplied with a low-level signal "0". The gate circuit 15 is turned on by the output signal of the OR gate 18 applied through the NOT gate 19. In other words, when the quantized signal 17 is "0" and the shift register 13 is in "0" state one scanning line before, the shift register 13 is rewritten by the shift register 14. Numeral 20 shows an OR gate, numeral 21 an AND gate, numeral 22 a NOT gate, and numeral 23 an R-S flip-flop. These elements 20, 21, 22 and 23 are arranged as shown so that the gate circuit 16 operates from the time when the quantized signal 17 is "1" or when the output of the shift register 13 is "1" and the quantized signal 17 is "1" until the output of the shift register 13 is reduced to "0", thus rewriting the data stored in the shift register 14 by the data stored in the shift register 33.

Figure 5:
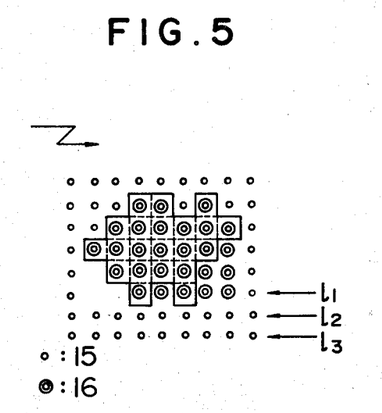
FIGS. 5 and 6 are diagrams for explaining the operation of the circuit shown in FIG. 4.

The diagram of FIG. 5 shows the operating points of the gate circuits 15 and 16. In FIG. 5, the mark ⤴ shows the direction of scanning. The part surrounded by the solid line shows a pattern. The mark ○ shows the operating point of the gate circuit 15, namely, the scanning point of the pattern at the time of transfer of the data in the shift register 14 to the shift register 13. The mark ⊙ shows the operating point of the gate circuit 16, namely, the scanning position of the pattern at the time of transfer of the data stored in the shift register 13 to the shift register 14.

Figure 6:
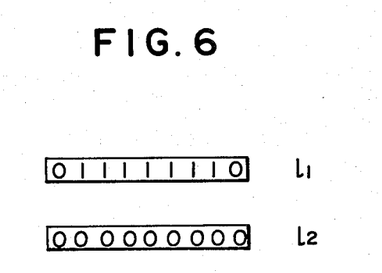

The symbol l₁ in FIG. 6 shows the data stored in the shift register 13 at the end of scanning of the scanning line l₁ in FIG. 5, and the symbol l₂ the data stored in the shift register 13 at the end of scanning of the scanning line l₂. As is obvious from FIG. 6, bits "1" are stored in the shift register 13 when a pattern exists in the scanning direction in FIG. 5, and then at the end of the pattern scanning, the data for reducing these bits to "0" are stored in the shift register 13. Turning back to FIG. 4, the output of the shift register 13 is applied to the shift register 24 having the same length as the scanning line, so that the output of the shift register 24 and a signal representing the reversal of the output of the shift register 13 are applied to the AND gate 25, thus producing a signal 26 synchronous with the scanning in the region corresponding to the horizontal direction of the pattern ended. This signal 26 is a pattern feature calculation signal for determining the feature of the pattern. On the other hand, the signal 26 is also applied to a D-type flip-flop 27, so that the signal representing the reversal of the signal 26 and the output of the flip-flop 27 are applied to the AND gate 28. As a result, one signal 29 is produced after production of the pattern feature calculation signal 26 in accordance with the pattern. This signal 29 makes up a decision start signal for actuating the defect decision circuit 11 after calculation of the pattern feature. It should be remembered that as seen from FIGS. 4 to 6 the pattern feature calculation signal 26 and the decision start signal 29 are produced when the pattern scanning is positioned on the scanning line l₃. That is, the time delay of one scanning line is involved.

Figure 7:
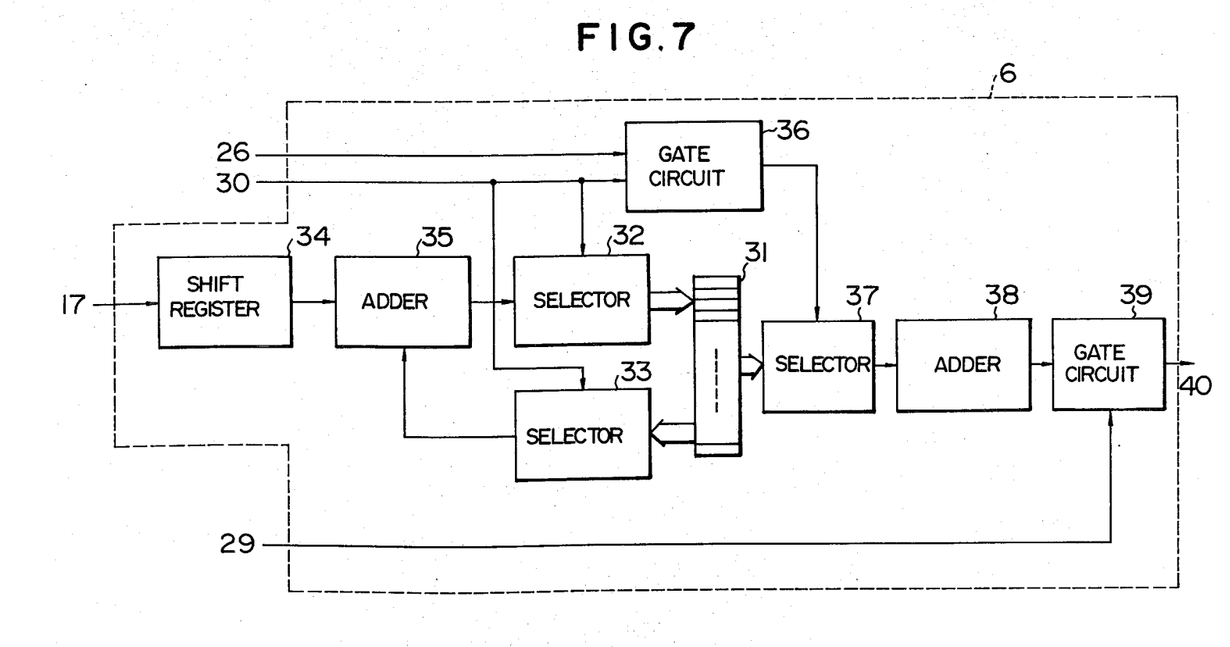
FIG. 7 is a diagram showing an embodiment of an area calculation circuit in FIG. 3.

An embodiment of the area calculation circuit 6 in FIG. 3 is shown in FIG. 7. In this diagram, numeral 30 shows an abscissa signal produced from the abscissa generator circuit 3, and numeral 31 shows an area calculation memory having a storage capacity corresponding to the length of the scanning line. The selector circuits 32 and 33 are actuated by the abscissa signal 30 thereby to make access to the address in the area calculation memory 31 corresponding to the scanning position. Numeral 34 shows a shift register corresponding to the length of the scanning line, which register is adapted to correspond to the time delay of the decision start signal 29 and the pattern feature calculation signal 26. The output of the shift register 34 is applied to the adder circuit 35. The adder circuit 35 is for adding the data stored in the area calculation memory 31 corresponding to the scanning position and the output of the shift register 34 to each other, and writing the sum thereof again in the area calculatoin memory 31. Numeral 36 shows a gate circuit. Only when an output signal is produced from the pattern feature calculation signal 26, the abscissa signal 30 is applied via the gate 36 to the selector circuit 37, thus reading out the data stored in the area calculation memory 31 of an address corresponding to the abscissa signal 30. The data thus read out is applied to the adder circuit 38, and the data in the area calculation memory continue to be added in the adder circuit 38 while the pattern feature calculation signal 26 is produced. When the output of the pattern feature calculation signal 26 stops being produced, namely, when an output signal is produced from the decision start signal 29, the gate circuit 39 is turned on, so that the area of the pattern ended is produced in the form of area signal 40 which is transferred to the defect decision circuit 11.

Figure 8:
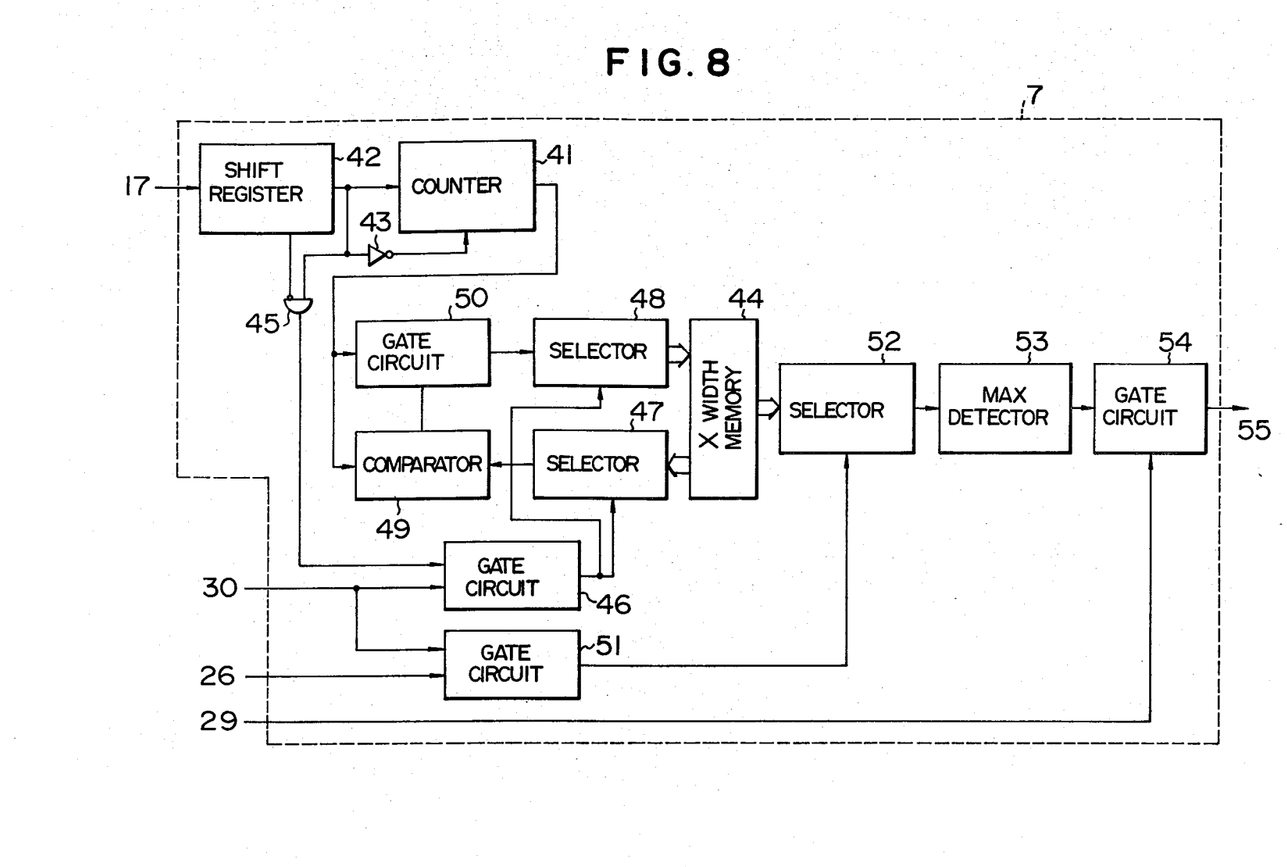
FIG. 8 shows an embodiment of an X width calculation circuit in FIG. 3.
Figure 9:
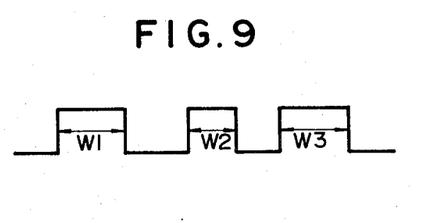
FIGS. 9 and 10 are diagrams for explaining the operation of the circuit shown in FIG. 8.
Figure 10:
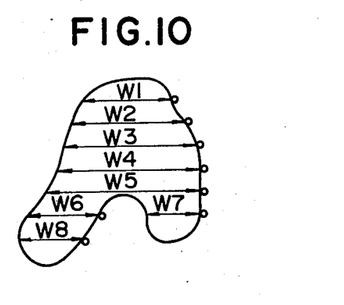

An embodiment of the maximum X width calculation circuit 7 in FIG. 3 is shown in FIG. 8. In this diagram, numeral 41 shows a counter circuit which, in response to the quantized signal 17 from the threshold circuit 2 through the shift register 42 corresponding to the length of the scanning line, counts the length of the successive "1" signals produced from the shift register 42. When the output of the shift register 42 becomes "0", this "0" signal is applied via the NOT gate 43 to the clear input terminal of the counter circuit 41, thus clearing the counter circuit 41. In other words, when the quantized signal 17 as shown in FIG. 9 is produced from the shift register 42, the counter circuit 41 determine the values $W_1$, $W_2$, $W_3$ and so on sequentially. Numeral 44 shows an X width memory having such a capacity as to store the maximum length at the position where the successive "1" of the output of the shift register 42 end and change to "0", the capacity being associated with the length of the scanning line. Specifically, in response to the output of the gate 45 which is produced when the input to the counter circuit 41 from the shift register 42 is "1" and the next output of the shift register 42 is "0", the abscissa signal 30 is passed through the gate circuit 46, so that the abscissa signal produced from the gate circuit 46 actuates the selector circuits 47 and 48. The output of the selector circuit 47 is applied to the comparator circuit 49 and compared with the data in the counter circuit 41. If the data in the counter circuit 41 is larger, the gate circuit 50 is actuated, so that the data in the X width memory 44 is rewritten by the data of the counter circuit 41 through the selector circuit 48. The pattern feature calculation signal 26 actuates the gate circuit 51 thus applying the abscissa signal 30 to the selector circuit 52. During the time when the pattern feature calculation signal 26 is produced, the data of the memory 44 are sequentially read out and applied to the maximum detection circuit 53. Thus the maximum value of the data of the memory 44 corresponding to the length of the ended pattern region along the X axis is determined, and the gate circuit 54 is actuated by the decision start signal 29, so that the maximum value of the width of a pattern along the X axis is transferred to the defect decision circuit 11 as the maximum X width signal 55. This indicates that the maximum value of Wi (i being 1 to 8 in this case) is applied to the defect decision circuit 11. In FIG. 10, circles show the positions where the values Wi are determined by the counter circuit 41. The data of the memory 44 corresponding to the circles are read out thereby to actuate the comparator circuit 49.

Figure 11:
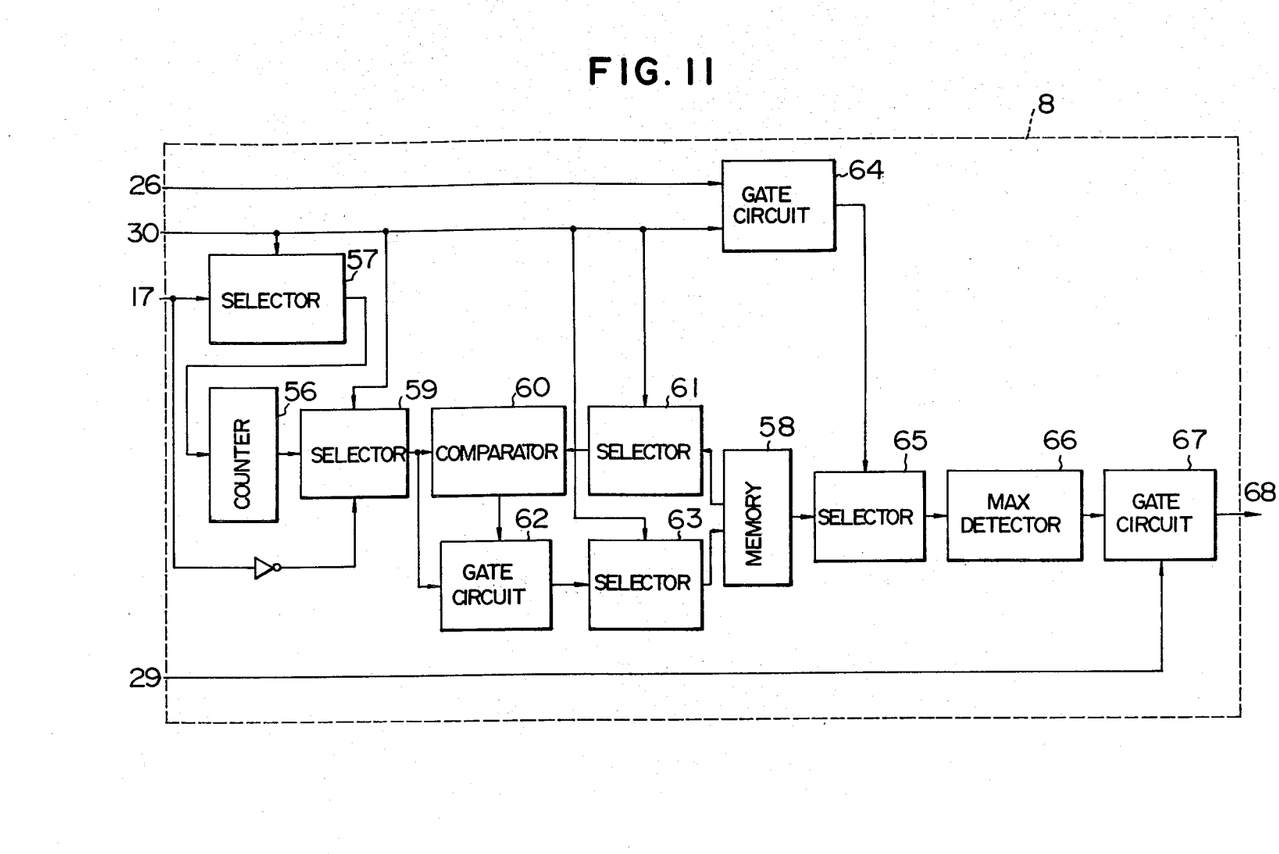
FIG. 11 shows an embodiment of a Y width calculation circuit in FIG. 3.
Figure 12:
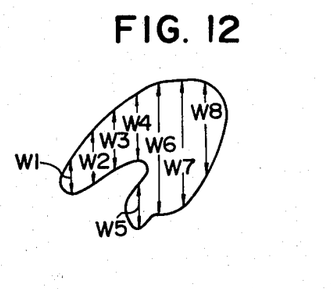
FIG. 12 is a diagram for explaining the operation of the circuit shown in FIG. 11.

An embodiment of the maximum Y width calculation circuit 8 of FIG. 3 is shown in FIG. 11. In this drawing, numeral 56 shows a counter provided corresponding to the length of the scanning line. Through the selector circuit 57 actuated by the abscissa signal 30, the quantized signal is applied to and counted in the counter selected by the selector circuit 57. Numeral 58 shows a Y width memory having a capacity corresponding to the length of the scanning line. Numeral 59 shows a selector circuit adapted to be actuated when the quantized signal 17 is "0", and applies to the comparator circuit 60 the data in the counter 56 corresponding to the abscissa signal 30. When the data of the counter 56 are produced, the comparator circuit 60 is supplied with the data of the memory 58 corresponding to the abscissa signal 30 through the selector circuit 61. When the data of the counter 56 is larger, the output of the comparator 60 is applied to the gate circuit 62, so that the data of the counter 56 are transferred to the memory 58 through the selector circuit 63, thus rewriting the data of the memory 58. This process will be explained with reference to the pattern of FIG. 12. Assume that the value $W_4$ is stored in the memory 58 and that $W_5$ is larger than $W_4$ when the value $W_5$ is determined by the counter 56. It means that the data of the memory 58 is rewritten from $W_4$ to $W_5$. Turning back to FIG. 11, the data of the memory 58 is applied to the maximum value detector circuit 66 when the abscissa signal 30 is applied to the selector circuit 65 by the actuation of the gate circuit 64 in response to the pattern feature calculation signal 26 indicating the end of the pattern. The maximum value Wy obtained at the maximum value detector circuit 66 is applied to the defect decision circuit 11 as a pattern Y maximum width signal 68 by the actuation of the gate circuit 67 in response to the decision start signal 29. In other words, the maximum value of Wi (i=1 to 8) in FIG. 12 is transferred to the defect decision circuit 11.

Figure 13:
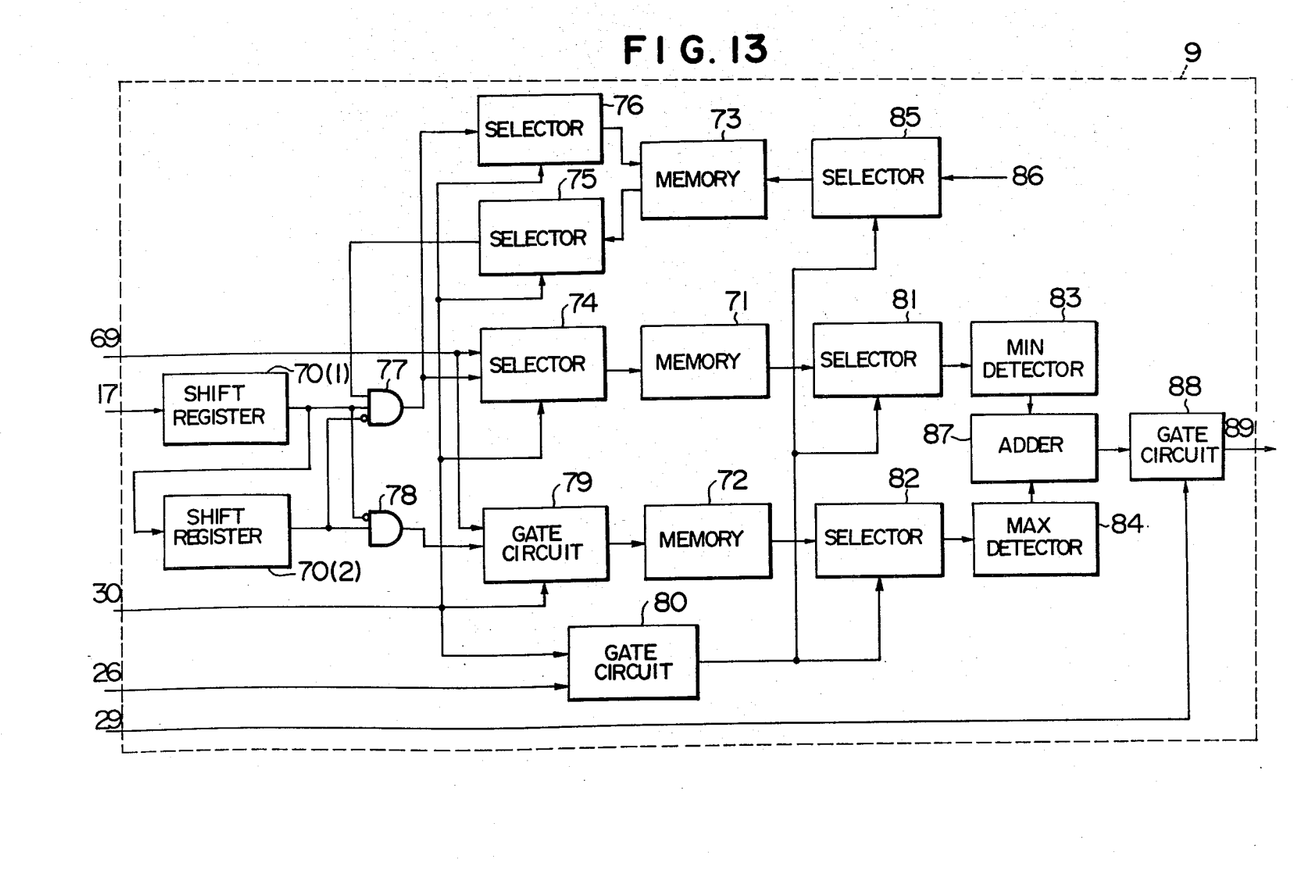
FIG. 13 shows an embodiment of a Y length calculation circuit in FIG. 3.
Figure 14:
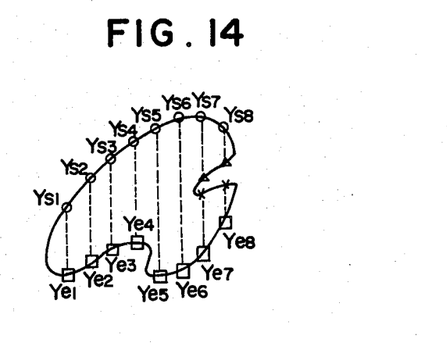
FIG. 14 is a diagram for explaining the operation of the circuit of FIG. 13.

An embodiment of the Y region length calculation circuit 9 of FIG. 3 is shown in FIG. 13. In this drawing, numeral 69 shows an ordinate signal produced from the ordinate generator circuit 4. Numerals 70(1) and 70(2) show two-stage shift registers corresponding to the length of the scanning line. Numerals 71 and 72 show memories having a capacity corresponding to the lengths of the scanning lines respectively for storing the starting ordinate Ysi (i=1 to 8) and the end ordinate Yei (i=1 to 8) of the pattern shown in FIG. 14 respectively. Numeral 73 shows a memory having a capacity corresponding to the length of the scanning line for storing the data on whether or not the value Ysi has already been detected. The fact that the output of the shift register 70(1) is "1" and the output of the shift register 70(2) is "0" shows that the point indicated by the circle or x in the pattern in FIG. 14 is being scanned. If the data of the memory 73 is such that the value Ysi has not yet been detected, namely, if it is a point as shown by the circle, then the ordinate signal 69 involved is written in the memory 71. Numerals 74, 75 and 76 show selector circuits for selecting the memories 71 and 73 corresponding to the abscissa signal 30. Numeral 77 shows a gate signal for producing a signal indicating that the value Ysi has been detected. Upon detection of Ysi, the memory 73 writes therein the data on Ysi detection through the selector circuit 76. The ordinate signal 69 associated with the time point when the output of the shift register 70(1) is "0" and the output of the shift register 70(2) is "1", namely, when the points of □ and Δ in FIG. 14 are being scanned is written in the memory 72 through the gate circuits 78 and 79. As shown in FIG. 14, the ordinate at mark Δ is written in the memory 72, which is rewritten at the position marked with □ (Ye7, Ye8). The data of the memories 71 and 72 are read out when the abscissa signal 30 passes through the gate circuit 80 to actuate the selector circuits 81 and 82 in response to the pattern feature calculation signal 26, and the respective data are applied to the minimum value detector circuit 83 and the maximum value detector circuit 84 respectively. Also, the fact that the pattern feature calculation signal 26 has passed the gate circuit 80 causes the selector circuit 85 to be actuated, so that the reset signal 86 is transferred to the memory 73 corresponding to the abscissa, thus resetting the condition that the value Ysi is detected. The minimum value min(Ysi) obtained from the minimum detector circuit 83 and the maximum value max(Ysi) obtained at the maximum value detector circuit 84 are applied to the subtractor circuit 87 for subtracting min(Ysi) from max(Ysi). At the time point when the decision start signal 29 is produced, the gate circuit 88 is turned on and the signal 29 is applied to the defect decision circuit 11 as the pattern Y region length signal 89. In FIG. 13, the values of Ysi and Yei actually obtained are Ysi+1 and Yei+2 respectively, which does not pose any problem since Ly=max(Yei)−min(Ysi)+1.

Figure 15:
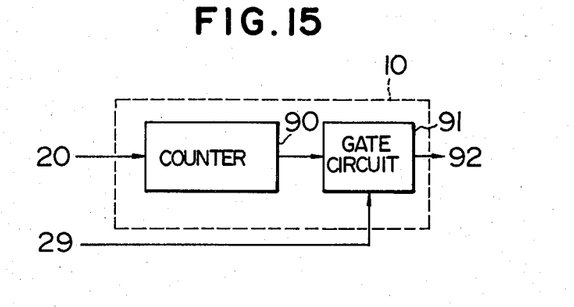
FIG. 15 is a diagram showing an embodiment of an X length calculation circuit in FIG. 3.

An embodiment of the X region length calculation circuit 10 of FIG. 3 is shown in FIG. 15. The length Lx of the pattern along X axis can be determined by counting the pattern feature calculation signal 26 indicating the end of the pattern. In FIG. 15, numeral 90 shows a counter circuit which in response to the pattern feature calculation signal 26 opens the gate circuit 91 by the decision start signal 29, so that the data stored in the counter circuit 90 is transferred to the defect decision circuit 11 as the signal 92 representing the region length of the pattern along X axis.

Figure 16:
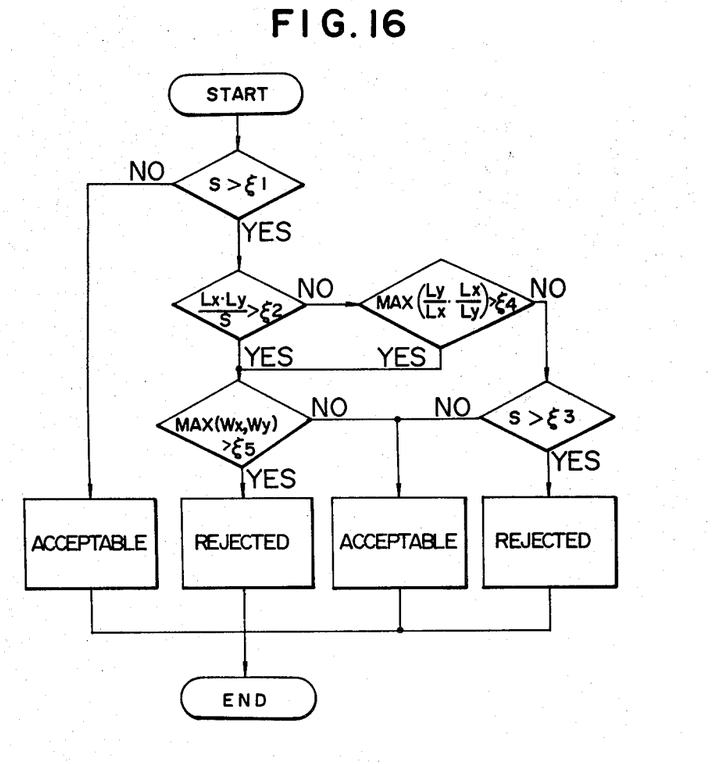
FIG. 16 is an operation flowchart of a defect decision circuit in FIG. 3.
Figure 17A:
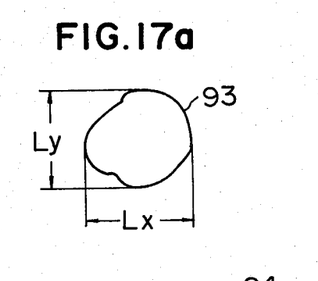
FIGS. 17a–17c diagrams showing a pattern example used for explaining the flowchart of FIG. 16.
Figure 17B:
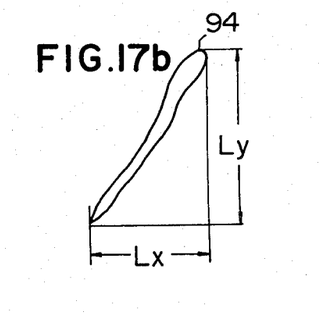
Figure 17C:
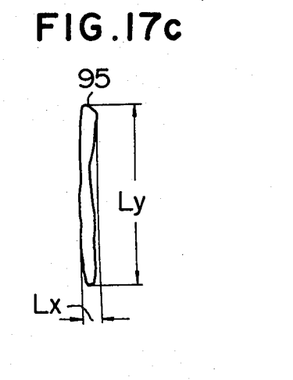

An embodiment of the defect decision circuit 11 will be described with reference to the operation flowchart of FIG. 16. In this embodiment, two defect patterns including a substantially circular pit like 93 in FIG. 17a and elongate cracks like 94 and 95 in FIGS. 17b and 17c are assumed to be involved. Patterns having an area more than a predetermined value $\epsilon_1$ are classified into pit and crack. In the case of a pit, it is decided whether the pit is a tolerable defect depending on whether its area is larger or smaller than a predetermined value $\epsilon_3$, and in the case of crack, it is decided whether the crack is a tolerable defect depending on whether its width is larger or smaller than a predetermined value $\epsilon_5$. The defect decision circuit 11 is actuated by the decision start signal 29 (FIG. 4) and receives as an input the area signal 40 (FIG. 7). The area S thus received is compared with the value $\epsilon_1$, and when S is smaller than or equal to $\epsilon_1$, the pattern is determined to be acceptable. When S is larger than $\epsilon_1$, on the other hand, the value Lx·Ly/S is compared with a predetermined value $\epsilon_2$ ($\epsilon_2 \geq 1$). If Lx·Ly/S is larger than $\epsilon_2$ (that is, when the pattern 94 as shown in FIG. 17b is involved), it is decided that there is a crack. If Lx·Ly is smaller than or equal to $\epsilon_2$ (such as when the pattern 93 or 95 shown in FIG. 17a or 17c respectively is involved), on the other hand, MAX(-Ly/Lx, Lx/Ly) is compared with a predetermined value $\epsilon_4$ ($\epsilon_4 \geq 1$) (which is equivalent to the checking of the ratio between longitudinal and lateral sides of the pattern), and if the former is larger than the latter, it is decided that a crack exists. If the former is smaller than the latter, on the other hand, it is decided that a pit is present. When it is decided that the defect is a pit, the area S thereof is compared with the value $\epsilon_3$, and if S is larger than $\epsilon_3$, it is rejected, while S is smaller than or equal to $\epsilon_3$, it is considered acceptable. In the last-mentioned case, the width MAX(Wx, Wy) thereof is compared with $\epsilon_5$, and if the former is larger than the latter, it is rejected, while if the former is smaller than or equal to the latter, it is considered acceptable. The process of FIG. 16 may be performed either by way of a circuit configuration or by computer software.

It will be understood from the foregoing description that according to the present invention even in the case where there are a plurality of independent patterns on the screen, the feature of each pattern is extracted thereby to decide on a defect of the pattern.

What is claimed is:

1. A surface defect inspection system comprising:
an image pick-up means for picking up an image by sequentially raster scanning the surface of an object two-dimensionally in abscissa and ordinate directions;
threshold means for quantizing an image signal produced from said image pick-up means as a binary signal in accordance with a predetermined threshold and sampling the quantized signal;
register means having a storage capacity corresponding to at least one raster scan line for sequentially and temporarily storing the sampled quantized signal delivered from said threshold means;
holding means for, when the sampled quantized signal corresponding to a defect pattern is delivered from said threshold means
for the first time at a certain abscissa in a certain ordinate corresponding to a certain raster scan line, holding the sampled quantized signal corresponding to the defect pattern at a portion corresponding to the abscissa of the corresponding defect pattern in said register means during succeeding scanning operations in the ordinate direction as long as the sampled quantized signal delivered from said threshold means includes at least one quantized signal corresponding to a defect pattern in an abscissa area having an abscissa of the defect pattern where said register means includes quantized signals corresponding to a defect pattern continuously in the abscissa direction, in each of succeeding raster scan lines;
pattern region end decision means for deciding that the defect pattern region has ended in the ordinate direction when the sampled quantized signal delivered from said threshold means includes no quantized signal corresponding to a defect pattern in the abscissa area having an abscissa of the defect pattern in a succeeding raster scan line;
pattern feature extracting means for extracting features of the defect pattern in accordance with the sampled quantized signal delivered from said threshold means in synchronism with the scanning in the abscissa direction;
memory means having a storage capacity corresponding to at least one raster scan line for temporarily and sequentially storing the result of the calculation delivered from said pattern feature extracting means to a storage area corresponding to the abscissa where the defect pattern exists;
reading means for, when said pattern region end decision means decides that the defect pattern region has ended in the ordinate direction, reading the features of the defect pattern from the storage area of said memory means corresponding to the abscissa where the defect pattern exists; and
defect decision means for comparing the features of each of the defect patterns separately read out of said reading means with a predetermined reference to thereby decide whether the defect pattern is acceptable or not.

2. A surface defect inspection system according to claim 1, wherein said holding means comprises a first shift register forming said register means so as to be able to shift said input sampled quantized signal, and a logical circuit for obtaining a logic combination between said sampled quantized signal delivered from said threshold means and a sampled quantized signal delivered from said shift register.

3. A surface defect inspection system according to claim 2, wherein said pattern region end decision means further comprises:
second shift register having a storage capacity corresponding to at least one raster scan line capable of storing no sampled quantized signal corresponding to the defect pattern when no sampled quantized signal corresponding to the defect pattern is delivered from said threshold means;
first rewriting means for rewriting the second shift register by the contents of said first shift register when the sampled quantized signal corresponding to the defect pattern is delivered from said first shift register, and from the time when the sampled quantized signals corresponding to the defect pattern are delivered from both of said threshold means and said first shift register, to the time when the output signal from said first shift register is changed from the sampled quantized signal to no sampled quantized signal corresponding to the defect pattern; and second rewriting means for rewriting the contents of the second shift register when no sampled quantized signals corresponding to the defect pattern are delivered from both of said threshold means and said first shift register.

4. A surface defect inspection system according to claim 2, wherein said pattern region end decision means further comprises a third shift register having a storage capacity corresponding to at least one raster scan line for storing the sampled quantized signal delivered from the first shift register, and a logical circuit for obtaining a logic combination between the sampled quantized signal delivered from the first shift register and the sampled quantized signal delivered from the third shift register.

5. A surface defect inspection system according to claim 1, wherein when the feature of the defect pattern is an area thereof, said pattern feature extracting means calculates the sampled quantized signal delivered from said threshold means for each abscissa through calculating means, and said memory means stores the result of the calculation delivered from said calculating means for each abscissa.

6. A surface defect inspection system according to claim 1,
wherein said pattern feature extracting means extracts the area of a pattern, the region length and the maximum width of the pattern along X axis and the region length and the maximum width of the pattern along Y axis as a feature thereof, from the binary signal delivered from said threshold means, and
wherein said defect decision means classifies patterns having an area larger than a predetermined value $\epsilon_1$ into pits and cracks, and includes means deciding that a pit having an area smaller than a predetermined value $\epsilon_3$ is a tolerable defect, said means deciding that a crack having a maximum width smaller than a predetermined value $\epsilon_5$ is a tolerable defect.

7. A surface defect inspection system according to claim 6, wherein defects are classified into pits and cracks by use of a ratio between the product of the region lengths of the pattern along X and Y axes respectively and the area of the pattern, and the ratio of the region lengths of the pattern along X and Y axes.

8. A surface defect inspection system comprising image pick-up means for picking up an image of a surface of an object including defect patterns by sequentially scanning the surface of an object line by line, binary converter means for converting the image signal produced from said image pick-up means into a binary code signal which represents the patterns on the surface, means for extending each pattern in a direction perpendicular to the direction of scan line to an end scan line for the pattern beyond which the pattern no longer exists and combining extended patterns, when they overlap to each other during said extending, into one extended pattern, pattern feature extracting means for extracting features of each extended pattern including at least one pattern in synchronism with the scanning, and for temporarily storing the features being extracted, pattern region end detection means for detecting the end scan line of each extended pattern, and defect discrimination means for reading out from said pattern feature extracting means the features of the extended pattern upon detection of the end scan line of the extended pattern, comparing the features of each extended pattern with at least one predetermined reference, and discriminating the extended pattern according to a predetermined classification based on the result of said comparison.

9. A surface defect inspection system according to claim 8, wherein said pattern region end detection means generates an end signal at each position of the end scan line corresponding to the width of the extended pattern.

10. A surface defect inspection system according to claim 8, wherein said pattern feature extracting means extracts the area of a pattern, the lengths of the pattern and the extended pattern in the directions along the scan line and perpendicular to the scan line.

11. A surface defect inspection system according to claim 8, wherein said defect discriminating means classifies patterns having an area larger than a predetermined value $\epsilon_1$ into pits and cracks, said means deciding that a pit having an area smaller than a predetermined value $\epsilon_3$ is a tolerable defect, said means deciding that a crack having a maximum width smaller than a predetermined value $\epsilon_5$ is a tolerable effect.

12. A surface defect inspection system according to claim 9, wherein defects are classified into pits and cracks by use of the ratio of the product of the lengths of the extended pattern along the two directions to the area of the pattern, and the ratio of the lengths of the pattern along the two directions.

* * * * *